United States Patent
Kantzes et al.

(10) Patent No.: US 9,201,414 B2
(45) Date of Patent: Dec. 1, 2015

(54) INTRINSICALLY-SAFE HANDHELD FIELD MAINTENANCE TOOL WITH IMAGE AND/OR SOUND CAPTURE

(75) Inventors: Christopher P. Kantzes, Minneapolis, MN (US); Brad N. Mathiowetz, Lakeville, MN (US); Todd M. Toepke, Eden Prairie, MN (US); Kun Yang, Eden Prairie, MN (US); Adam E. Lund, St. Louis Park, MN (US); Donald R. Lattimer, Chaska, MN (US); Brian A. Franchuk, Richfield, MN (US)

(73) Assignee: Fisher-Rosemount Systems, Inc., Austin, TX (US)

( * ) Notice: Subject to any disclaimer, the term of this patent is extended or adjusted under 35 U.S.C. 154(b) by 533 days.

(21) Appl. No.: 13/191,604

(22) Filed: Jul. 27, 2011

(65) Prior Publication Data
US 2012/0038760 A1    Feb. 16, 2012

Related U.S. Application Data

(60) Provisional application No. 61/368,477, filed on Jul. 28, 2010.

(51) Int. Cl.
*H04N 7/18* (2006.01)
*G05B 19/042* (2006.01)

(52) U.S. Cl.
CPC .......... *G05B 19/042* (2013.01); *G05B 19/0426* (2013.01); *G05B 2219/23018* (2013.01); *G05B 2219/23054* (2013.01); *G05B 2219/23126* (2013.01); *G05B 2219/23163* (2013.01); *G05B 2219/23406* (2013.01); *G05B 2219/23445* (2013.01); *G05B 2219/23446* (2013.01); *G05B 2219/24001* (2013.01);

(Continued)

(58) Field of Classification Search
USPC ................................................ 348/61; 455/41
See application file for complete search history.

(56) References Cited

U.S. PATENT DOCUMENTS

| 5,195,392 A | 3/1993 | Moore et al. ................. 73/866.5 |
| 5,309,351 A | 5/1994 | McCain et al. ............... 364/132 |

(Continued)

FOREIGN PATENT DOCUMENTS

| CN | 101763576 | 6/2010 |
| CN | 201518523 U | 6/2010 |

(Continued)

OTHER PUBLICATIONS

Invitation to Pay Additional Fees for international patent application No. PCT/US2010/034889 dated Sep. 15, 2010.

(Continued)

*Primary Examiner* — Dave Czekaj
*Assistant Examiner* — Leron Beck
(74) *Attorney, Agent, or Firm* — Christopher R. Christenson; Kelly, Holt & Christenson, PLLC

(57) ABSTRACT

An intrinsically-safe handheld field maintenance tool includes a process communication module configured communicatively couple to a field device. A camera is configured to obtain at least one image relative to the field device. A controller is coupled to the process communication module and operably coupled to the camera. The controller is configured to store the at least one image relative to the field device. The handheld field maintenance tool may also include or employ an audio input device to capture audio files.

7 Claims, 7 Drawing Sheets

(52) U.S. Cl.
CPC .............. *G05B 2219/24056* (2013.01); *G05B 2219/25062* (2013.01); *G05B 2219/25428* (2013.01); *G05B 2219/31121* (2013.01); *G05B 2219/31197* (2013.01); *G05B 2219/31475* (2013.01); *G05B 2219/32007* (2013.01); *G05B 2219/32144* (2013.01); *G05B 2219/32226* (2013.01); *G05B 2219/33331* (2013.01); *G05B 2219/35422* (2013.01); *G05B 2219/35429* (2013.01); *G05B 2219/36122* (2013.01); *G05B 2219/36128* (2013.01)

(56) References Cited

U.S. PATENT DOCUMENTS

| | | | |
|---|---|---|---|
| 5,442,632 A | 8/1995 | Burton et al. | 371/20.1 |
| 5,903,455 A | 5/1999 | Sharpe, Jr. et al. | 364/188 |
| 6,033,226 A | 3/2000 | Bullen | 434/219 |
| 6,205,239 B1 * | 3/2001 | Lin et al. | 382/149 |
| 6,211,649 B1 | 4/2001 | Matsuda | 320/115 |
| 6,236,223 B1 | 5/2001 | Brady et al. | 324/750.3 |
| 6,377,859 B1 | 4/2002 | Brown et al. | 700/79 |
| 6,629,059 B2 | 9/2003 | Borgeson et al. | 702/183 |
| 6,633,782 B1 | 10/2003 | Schleiss et al. | 700/26 |
| 6,725,182 B2 | 4/2004 | Pagnano et al. | 702/188 |
| 6,971,063 B1 | 11/2005 | Rappaport et al. | 715/733 |
| 7,013,184 B2 | 3/2006 | Romagnoli et al. | 700/17 |
| 7,117,122 B2 | 10/2006 | Zielinski et al. | 702/183 |
| 7,120,391 B2 | 10/2006 | Stengele et al. | 455/41.3 |
| 7,188,200 B2 | 3/2007 | Griech | 710/100 |
| 7,233,745 B2 * | 6/2007 | Loechner | 398/128 |
| 7,337,369 B2 | 2/2008 | Barthel et al. | 714/43 |
| 7,400,255 B2 | 7/2008 | Horch | 340/572.7 |
| 7,421,531 B2 | 9/2008 | Rotvold et al. | 710/315 |
| 7,454,252 B2 | 11/2008 | El-Sayed | 700/21 |
| 7,505,819 B2 | 3/2009 | El-Sayed | 700/21 |
| 7,506,812 B2 | 3/2009 | von Mueller et al. | 235/449 |
| 7,675,406 B2 | 3/2010 | Baier et al. | 340/506 |
| 7,733,833 B2 | 6/2010 | Kalika et al. | 370/338 |
| 7,797,061 B2 | 9/2010 | El-Sayed | 700/21 |
| 8,000,815 B2 | 8/2011 | John et al. | 700/18 |
| 8,036,007 B2 | 10/2011 | Woehrle | 363/65 |
| 8,059,101 B2 | 11/2011 | Westerman et al. | 345/173 |
| 8,060,862 B2 | 11/2011 | Eldridge et al. | 717/121 |
| 8,060,872 B2 | 11/2011 | Da Silva Neto | 717/177 |
| 8,074,172 B2 | 12/2011 | Kocienda et al. | 715/263 |
| 8,126,145 B1 | 2/2012 | Tewari et al. | 380/255 |
| 8,150,462 B2 | 4/2012 | Guenter et al. | 455/557 |
| 8,180,948 B2 | 5/2012 | Kreider et al. | 710/313 |
| 8,224,256 B2 | 7/2012 | Citrano, III et al. | 455/67.11 |
| 2001/0047504 A1 | 11/2001 | Aoyama | 714/799 |
| 2002/0004370 A1 | 1/2002 | Stengele et al. | 455/39 |
| 2002/0007237 A1 | 1/2002 | Phung et al. | 701/33 |
| 2002/0027504 A1 | 3/2002 | Davis et al. | 340/540 |
| 2002/0086642 A1 | 7/2002 | Ou et al. | 455/69 |
| 2002/0171558 A1 | 11/2002 | Bartelheim et al. | 340/825.49 |
| 2003/0050737 A1 | 3/2003 | Osann, Jr. | 700/276 |
| 2003/0109937 A1 | 6/2003 | Zielinski et al. | 700/1 |
| 2003/0204373 A1 | 10/2003 | Zielinski et al. | 702/184 |
| 2003/0229472 A1 | 12/2003 | Kantzes et al. | 702/183 |
| 2004/0039458 A1 | 2/2004 | Mathiowetz et al. | 700/17 |
| 2004/0093100 A1 | 5/2004 | Gleis | |
| 2004/0111238 A1 | 6/2004 | Kantzes et al. | 702/183 |
| 2004/0193287 A1 | 9/2004 | Lefebvre et al. | 700/1 |
| 2004/0204193 A1 | 10/2004 | Li et al. | 455/575.1 |
| 2004/0228184 A1 | 11/2004 | Mathiowetz | 365/202 |
| 2004/0230327 A1 | 11/2004 | Opheim et al. | 700/83 |
| 2005/0164684 A1 | 7/2005 | Chen et al. | 455/414.1 |
| 2005/0222698 A1 | 10/2005 | Eryurek et al. | 700/90 |
| 2005/0223120 A1 | 10/2005 | Scharold et al. | 710/1 |
| 2006/0014533 A1 | 1/2006 | Warren | 455/423 |
| 2006/0087402 A1 | 4/2006 | Manning et al. | 340/3.1 |
| 2006/0206277 A1 | 9/2006 | Horch | 702/82 |
| 2006/0290496 A1 | 12/2006 | Peeters | 340/572.1 |
| 2006/0291438 A1 | 12/2006 | Karschnia et al. | 370/338 |
| 2007/0161352 A1 | 7/2007 | Dobrowski et al. | 455/69 |
| 2007/0161371 A1 | 7/2007 | Dobrowski et al. | 455/423 |
| 2007/0179645 A1 | 8/2007 | Nixon et al. | 700/83 |
| 2007/0208279 A1 | 9/2007 | Panella et al. | 600/595 |
| 2007/0280507 A1 * | 12/2007 | Murali | 382/107 |
| 2008/0114911 A1 | 5/2008 | Schumacher | 710/72 |
| 2008/0234837 A1 | 9/2008 | Samudrala et al. | 700/19 |
| 2008/0268784 A1 | 10/2008 | Kantzes et al. | 455/66.1 |
| 2009/0065578 A1 | 3/2009 | Peterson et al. | 235/382 |
| 2009/0094466 A1 | 4/2009 | Matthew et al. | 713/300 |
| 2009/0111378 A1 * | 4/2009 | Sheynman et al. | 455/41.1 |
| 2009/0125713 A1 | 5/2009 | Karschnia et al. | 713/153 |
| 2009/0171483 A1 | 7/2009 | Scheuermann | 700/83 |
| 2009/0177970 A1 | 7/2009 | Jahl et al. | 715/735 |
| 2009/0228121 A1 | 9/2009 | Fujiwara et al. | |
| 2009/0271726 A1 | 10/2009 | Gavimath et al. | 715/771 |
| 2009/0284390 A1 | 11/2009 | Lahner et al. | 340/825.49 |
| 2009/0296601 A1 | 12/2009 | Citrano, Iii et al. | 370/254 |
| 2009/0326852 A1 | 12/2009 | Vetter et al. | 702/108 |
| 2010/0100766 A1 | 4/2010 | Bengtsson et al. | 714/23 |
| 2010/0114347 A1 | 5/2010 | Dheenathayalan et al. | 700/97 |
| 2010/0114549 A1 | 5/2010 | Kolavi | 703/13 |
| 2010/0145476 A1 | 6/2010 | Junk et al. | 700/7 |
| 2010/0150425 A1 * | 6/2010 | Kalteis | 382/141 |
| 2010/0220630 A1 | 9/2010 | Kalika et al. | 370/254 |
| 2010/0290084 A1 | 11/2010 | Russell, III et al. | 358/1.15 |
| 2010/0290351 A1 | 11/2010 | Toepke et al. | 370/250 |
| 2010/0290359 A1 | 11/2010 | Dewey et al. | 370/252 |
| 2010/0293363 A1 | 11/2010 | Meyer et al. | 713/1 |
| 2011/0117529 A1 | 5/2011 | Barash et al. | 434/265 |
| 2011/0238188 A1 | 9/2011 | Washiro | 700/19 |
| 2012/0038458 A1 | 2/2012 | Toepke et al. | 340/6.1 |
| 2012/0038548 A1 | 2/2012 | Toepke et al. | 345/156 |
| 2012/0040316 A1 | 2/2012 | Mathiowetz et al. | 434/219 |
| 2012/0040698 A1 | 2/2012 | Ferguson et al. | 455/457 |
| 2012/0041744 A1 | 2/2012 | Kantzes et al. | 703/13 |
| 2012/0046911 A1 | 2/2012 | Mathiowetz et al. | 702/184 |

FOREIGN PATENT DOCUMENTS

| | | |
|---|---|---|
| DE | 10245176 | 4/2004 |
| DE | 102007035158 | 1/2009 |
| DE | 102008029406 | 12/2009 |
| DE | 102009028195 | 2/2011 |
| EP | 1515208 | 3/2005 |
| EP | 1916582 | 4/2008 |
| EP | 2071427 | 6/2009 |
| EP | 2077473 | 7/2009 |
| EP | 2148259 | 1/2010 |
| EP | 2204705 | 7/2010 |
| GB | 2382418 | 5/2003 |
| GB | 2 394 124 | 4/2004 |
| JP | 9051583 | 2/1997 |
| JP | H11233965 | 8/1999 |
| JP | 2001337004 | 7/2001 |
| JP | 2004505337 | 2/2004 |
| JP | 2004265131 A | 9/2004 |
| JP | 2006285632 A1 | 10/2006 |
| JP | 2007-91381 | 4/2007 |
| JP | 2008165193 | 7/2008 |
| JP | 2009038544 | 2/2009 |
| KR | 20060078883 | 7/2006 |
| WO | WO 01/35190 | 5/2001 |
| WO | WO 02/086662 | 10/2002 |
| WO | WO 2006/016845 | 2/2006 |
| WO | WO 2008/042074 | 4/2008 |
| WO | WO 2008/077358 | 7/2008 |
| WO | WO 2008/096216 | 8/2008 |
| WO | WO 2008/127632 | 10/2008 |
| WO | WO 2009/003146 | 12/2008 |
| WO | WO 2009/003148 | 12/2008 |
| WO | WO2009026032 | 2/2009 |
| WO | WO 2009/074544 | 6/2009 |

OTHER PUBLICATIONS

ABB Limited: "Wireless Instrumentation Jargon Buster". Information bulletin instrumentation ABB no IB/INST-018, Mar. 3, 2009,

(56) References Cited

OTHER PUBLICATIONS

XP002596601. Retrieved from the Internet: URL:http://www05.abb.com/global/scot/scot203.nsf/veritydisplay/be00ec76ef07e978c125756e003157b9/$File/IB_INST_018_1.pdf.
Notification of Transmittal of the International Search Report and the Written Opinion from the International Application No. PCT/US2010/021764.
David Gustafsson: "WirelessHART—Implementation and Evaluation on Wireless Sensors". Masters's Degree Project, KTH University, Electrical Engineering, Apr. 1, 2009, pp. 1-39, XP002596602, Stockholm, Sweden. Retrieved from the Internet: URL:http://www.ee.kth.se/php/modules/publications/reports/2009/XR-EE-RT%202009:003.pdf.
Notification of Transmittal of the International Search Report and the Written Opinion for the International application No. PCT/US2010/034848 dated Aug. 26, 2010.
Possio Bluetooth to WLAN Gateway PX20: Full Product Description retrieved from http://www.blueunplugged.com/p.aspx?p=105816.
1420 Wireless Gateway: Product Data Sheet 00813-0100-4420, Rev BA Mar. 2008. Emerson Process Management.
Smart Wireless Gateway (WirelessHART™). Quick Installation Guide 00825-0200-4420, Rev BA. Aug. 2009. Emerson Process Management.
Rosemount 3051S Wireless Series Scalable Pressure, Flow, and Level Solutions. Reference Manual 00809-0100-4802, rev BA. Aug. 2007. Emerson Process Management.
EPO Communication pursuant to Rules 161(I) and 162 EPC for European patent application No. 10701430.0 dated Aug. 30, 2011.
Invitation to Pay Additional Fees for international patent application No. PCT/US2010/034949 dated Sep. 17, 2010.
Technical Data Sheet: VIATOR® USB HART® Interface (Model 010031). MACTek Measurement and Control Technologies.
VIATOR® Bluetooth® Wireless Technology Interface for use with HART field devices. MACTek Measurement and Control Technologies retrieved from www.mactekcorp.com/product5.htm.
Product Data Sheet: VIATOR RS232. MACTek Measurement and Control Technologies retrieved from www.mactekcorp.com/product1.htm.
Notification of Transmittal of the International Search Report and the Written Opinion from the International Application No. PCT/US2010/034889.
Notification of Transmittal of the International Search Report and the Written Opinion from the International Application No. PCT/US2010/034949.
EPO Communication from related European application No. 10730279.6 dated Jan. 13, 2012.
EPO Communication from related European application No. 10730281.2 dated Jan. 13, 2012.
EPO Communication from related European application No. 10725543.2 dated Jan. 12, 2012.
Rosemount 3051 SMV Quick Installation Guide 00825-0100-4803 Rev BA. Apr. 2011.
Invitation to Pay Additional Fees from the International Application No. PCT/US2011/045673 dated Jan. 16, 2012.
Notification of Transmittal of the International Search Report and the Written Opinion from the International Application No. PCT/US2011/045680 dated Jul. 6, 2012.
Notification of Transmittal of the International Search Report and the Written Opinion from the International Application No. PCT/US2011/045681 dated Jan. 5, 2012.
475 Field Communicator. User's Guide XP007919976. Aug. 2009. www.fieldcommunicator.com by Emerson Process Management.
1420 Wireless Gateway. Reference Manual 00809-0100-4420, Rev BA. Aug. 2007. Emerson Process Management.
Invitation to pay additional fees from the related International patent application No. PCT/US2011/045679 dated Aug. 6, 2012.
Invitation to pay additional fees from the related International patent application No. PCT/US2011/045664 dated Aug. 9, 2012.
Invitation to pay additional fees from the related International patent application No. PCT/US2011/045676 dated Jul. 30, 2012.
Lee S W et al: "Honam Petrochemical Corporation Uses Simulator for Ethylene Plant Operator Training", Processing of the Industrial Computing Conference. Houston, Oct. 18-23, 1992. pp. 219-222.
Kurrle H-P et al.: "Trainingssimulator Zur Ausbildung Von Chemikanten und Anlagenfahrern. Otraining Simulator for the Training of Process Workers (Chemikanten) and Operators", Automatisierungstechnische Praxis—ATP, Oldenbourg Indusrieverlag, Munchen, DE, vol. 36, No. 7, Jul. 1, 1994. Abstract, Section 2.
Invitation to pay additional fees from the related International patent application No. PCT/US2011/045665 dated Aug. 23, 2012.
Bushman J B: "Ally: An Operator's Associate for Cooperative Supervisory Control Systems", IEEE Transactions on Systems, Man and Cybernetics, IEEE Inc. New York, US, vol. 23, No. 1, Jan. 1, 1993, pp. 111-128.
First Communication for the related European patent application No. 107302812 dated Oct. 11, 2012.
International Search Report and Written Opinion from the related International patent application No. PCT/US2011/045664 dated Nov. 6, 2012.
International Search Report and Written Opinion from the related International patent application No. PCT/US2011/045679 dated Nov. 6, 2012.
International Search Report and Written Opinion from the related International patent application No. PCT/US2011/045665 dated Nov. 6, 2012.
First Communication from related European patent application No. 107255432 dated Oct. 11, 2012.
First Communication from related European patent application No. 107302796 dated Oct. 19, 2012.
Office Action from related Russian application No. 2011151063 dated Nov. 12, 2012.
First Office Action from related Japanese application No. 2015511048, dated Jan. 29, 2013.
First Office Action from counterpart Japanese patent application No. 2013-521969, dispatched on Jan. 28, 2014. 5 pages.
First Office Action from counterpart Chinese patent application No. 201180001615.0, issued Aug. 29, 2013. 14 pages.
Second Office Action from counterpart Chinese patent application No. 201180001615.0, Issued Feb. 26, 2014. 17 pages.
Notification Regarding Results of Examination on Patentability from Russian Application No. 2013108906, dated Jun. 24, 2014 with English Translation. 10 pages.
Office Action from Canadian Patent Application No. 2,806,244 dated Jul. 22, 2014. 3 pages.
Decision of Rejection from Japanese Application No. 2013-521969, dispatch date Sep. 16, 2014, 6 pages with English Translation.
Notification of Reasons for Rejection from corresponding Japanese patent application No. 2013-521969, from Sep. 15, 2015. [49 pages with English translation].
Communication pursuant to Article 94(3) EPC fromcorresponding European patent application No. 11739256.3, from Sep. 10, 2015, [5 pages].

\* cited by examiner

INTRINSICALLY-SAFE HANDHELD FIELD MAINTENANCE TOOL WITH IMAGE AND/OR SOUND CAPTURE

CROSS-REFERENCE TO RELATED APPLICATION

The present application is based on and claims the benefit of U.S. provisional patent application Ser. No. 61/368,477, filed Jul. 28, 2010, the content of which is hereby incorporated by reference in its entirety.

BACKGROUND

Handheld field maintenance tools are known. Such tools are highly useful in the process control and measurement industry to allow operators to conveniently communicate with and/or interrogate field devices in a given process installation. Examples of such process installations include petroleum, pharmaceutical, chemical, pulp, and other fluid processing installations. In such installations, the process control and measurement network may include tens or even hundreds of various field devices which periodically require maintenance to ensure that such devices are functioning properly and/or calibrated. Moreover, when one or more errors in the process control and measurement installation are detected, the use of a handheld field maintenance tool allows a technician to quickly diagnose such errors in the field. Handheld field maintenance tools are generally used to configure, calibrate, and diagnose problems relative to intelligent field devices using digital process communication protocols.

Since at least some process installations may involve highly volatile, or even explosive, environments, it is often beneficial, or even required, for field devices and the handheld field maintenance tools used with such field devices to comply with intrinsic safety requirements. These requirements help ensure that compliant electrical devices will not generate a source of ignition even under fault conditions. One example of Intrinsic Safety requirements is set forth in: APPROVAL STANDARD INTRINSICALLY SAFE APPARATUS AND ASSOCIATED APPARATUS FOR USE IN CLASS I, II and III, DIVISION NUMBER 1 HAZARDOUS (CLASSIFIED) LOCATIONS, CLASS NUMBER 3610, promulgated by Factory Mutual Research October, 1998. An example of a handheld field maintenance tool that complies with intrinsic safety requirements includes that sold under trade designation Model 475 Field Communicator, available from Emerson Process Management of Austin, Tex.

SUMMARY

An intrinsically-safe handheld field maintenance tool includes a process communication module configured communicatively couple to a field device. A camera is configured to obtain at least one image relative to the field device. A controller is coupled to the process communication module and operably coupled to the camera. The controller is configured to store the at least one image relative to the field device. The handheld field maintenance tool may also include or employ an audio input device to capture audio files.

DETAILED DESCRIPTION

Figure 1A:
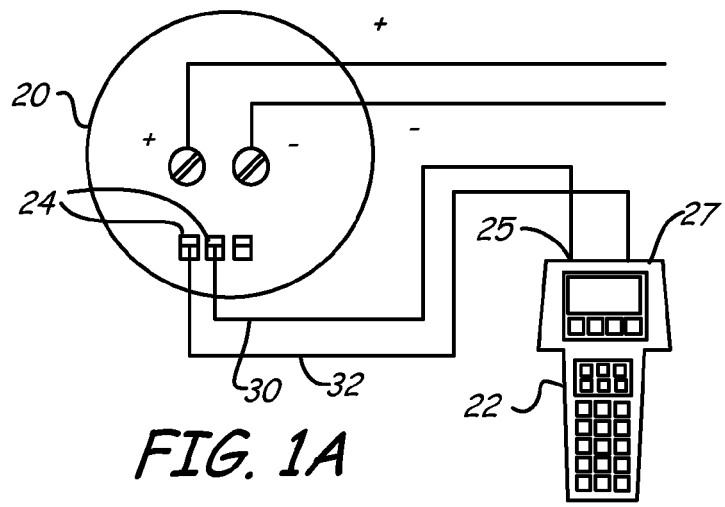
FIGS. 1A and 1B are diagrammatic views of a handheld field maintenance tool with which embodiments of the invention are particularly useful.
Figure 1B:
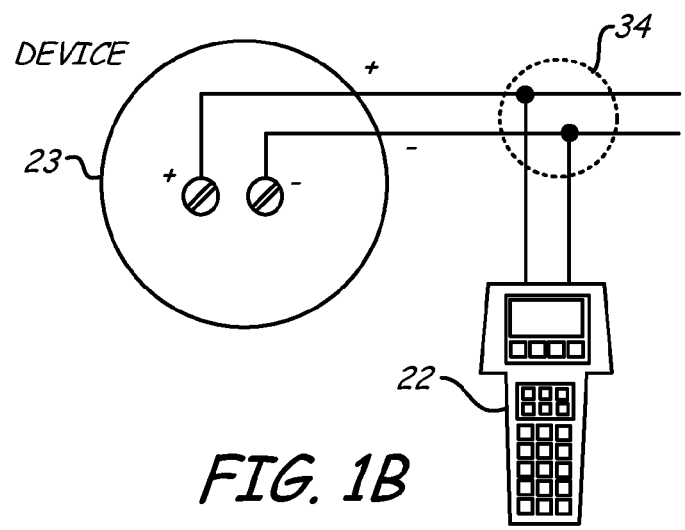

FIGS. 1A and 1B are diagrammatic views of a handheld field maintenance tool 22 coupled to field devices 20, 23. As shown in FIG. 1A, handheld field maintenance tool 22 includes a pair of terminals 25, 27 that couple to test leads 30, 32, respectively, which are then coupled to terminals 24 of field device 20. Terminals 24 may be dedicated terminals to allow such a handheld field maintenance tool to couple to device 20 and interact with device 20. The utilization of terminals 25, 27 to couple to field device illustrates an example of a wired connection between handheld field maintenance tool 22 and field device 20.

FIG. 1B shows an alternate arrangement where handheld field maintenance tool 22 couples directly to the process control loop 34 to which field device 23 is coupled. In either case, the wired connection between the handheld field maintenance tool and the field device allows the handheld field maintenance tool to interact with the desired field device 20, 23.

Figure 2:
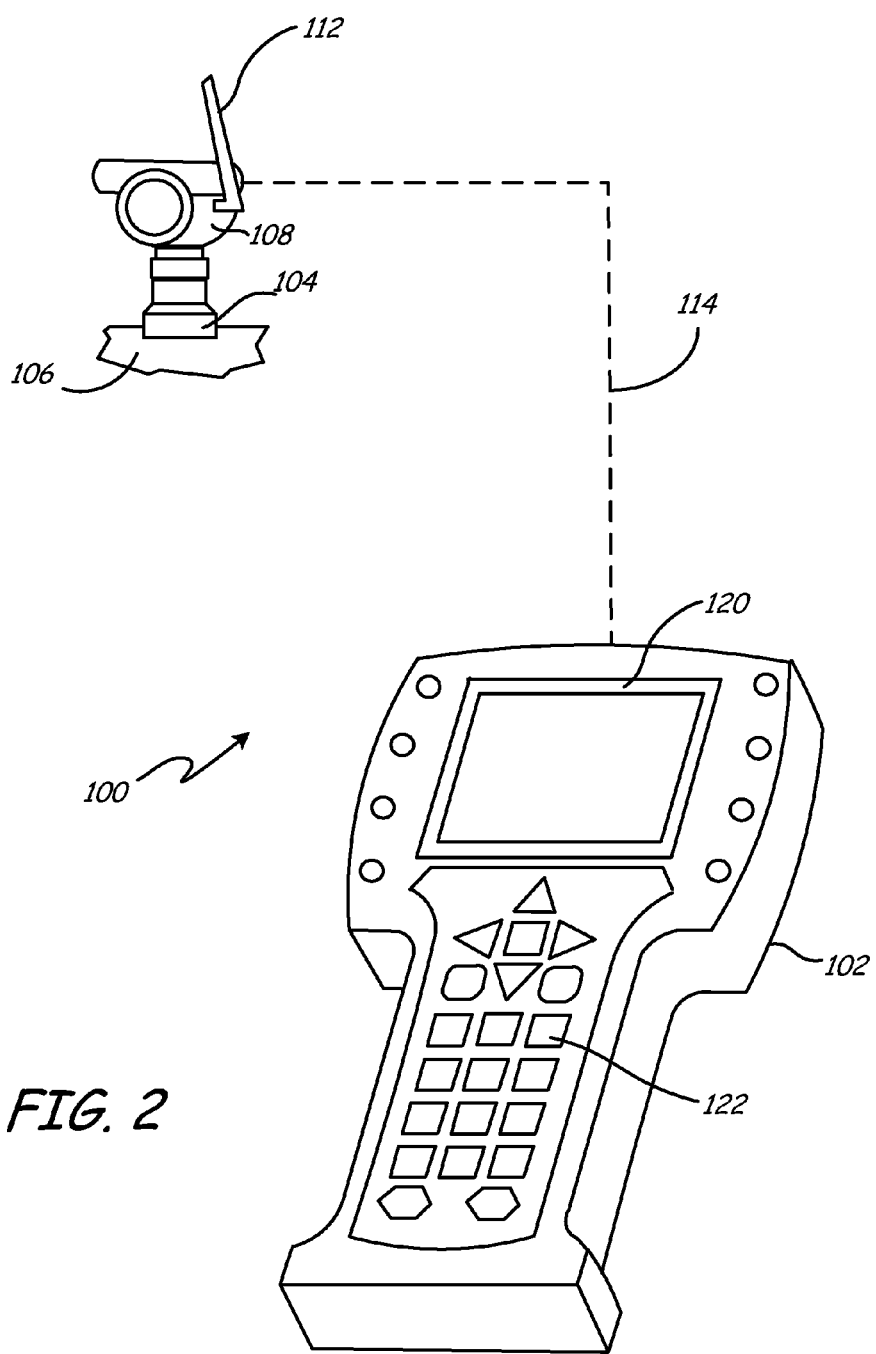
FIG. 2 is a diagrammatic view of a handheld field maintenance tool with which embodiments of the present invention are particularly useful.

FIG. 2 is a diagrammatic view of handheld field maintenance tool 102 interacting with wireless field device 104. System 100 includes handheld field maintenance tool 102 communicating with field device 104. Handheld field maintenance tool 102 is communicatively coupled to field device 104 via communication link 114. Communication link 114 can take any suitable form including wired connections as shown in FIGS. 1A and 1B, as well as wireless communication techniques that are currently being used or being developed. Handheld field maintenance tool 102 allows a technician to interact with field device 104 to configure, calibrate, and/or diagnose problems with respect to field device 104 using a digital process communication protocol such as FOUNDATION™ Fieldbus and/or the HART® protocol. Handheld field maintenance tools, such as tool 102 can be used to save configuration data from field devices, such as field device 104.

Field device 104 may be any device that senses a variable in the process and transmits information related to the variable over a process communication loop; such as a pressure or temperature. Field device 104 may also be a device that receives information from a process communication loop and sets a physical parameter, such as a valve closure, based on the information. Field device 104 is depicted as an industrial process fluid pressure transmitter having a pressure manifold 106 coupled thereto, and an electronics enclosure 108. Field device 104 is provided for illustrative purposes only. In reality, field device 104 may be any industrial device, such as a process fluid temperature transmitter, process fluid level transmitter, process fluid flow transmitter, valve controller, or any other device that is useful in the measurement and/or control of industrial processes.

Handheld field maintenance tool 102 generally includes a user interface that comprises a display 120 as well as a number of user input buttons 122. Display 120 may be any suitable display such as an active-matrix liquid crystal display, or any other suitable display that is able to provide useful information. Buttons 122 may comprise any suitable arrangement of buttons relative to any number of functions to which the handheld field maintenance tool may be directed. Buttons 122 may comprise a numeric keypad, an alphanumeric keypad, any suitable number of custom functions and/or navigation buttons, or any combination thereof.

Figure 3:
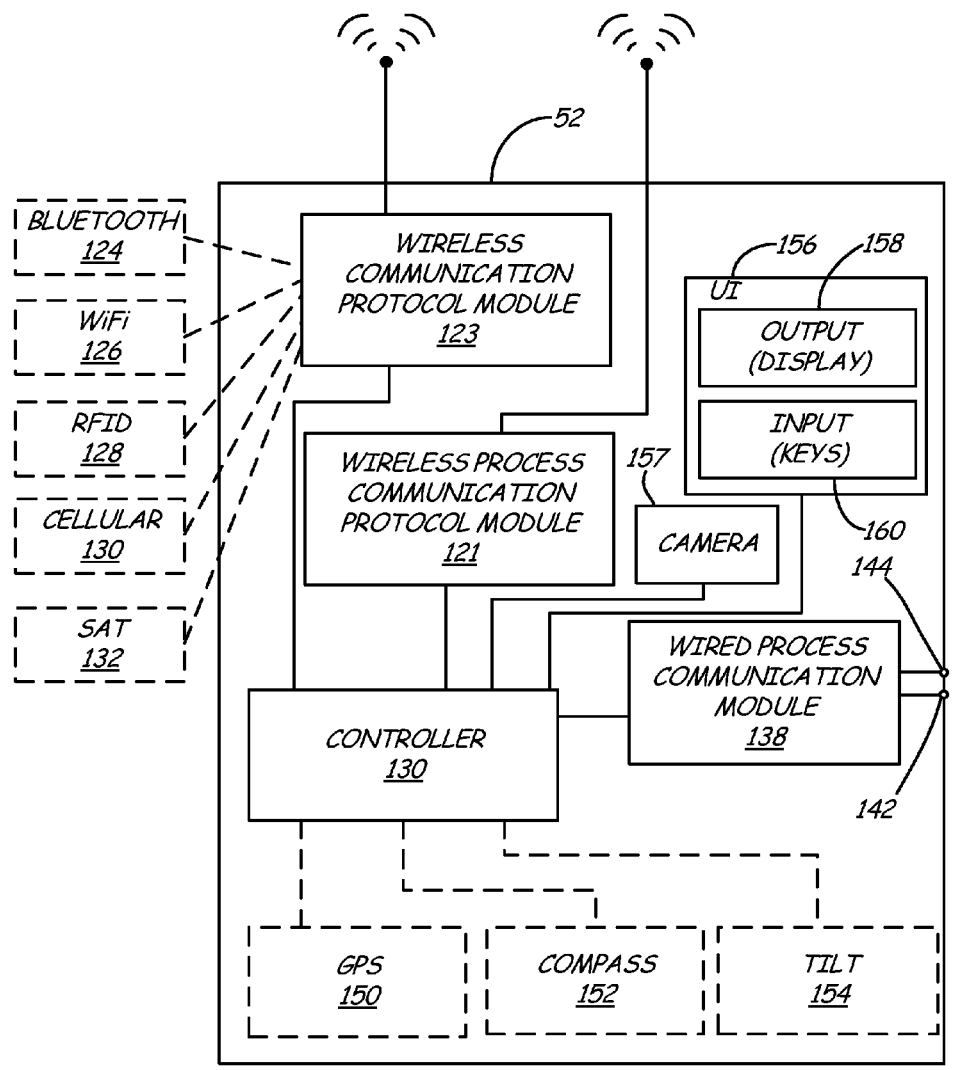
FIG. 3 is a block diagram of a handheld field maintenance tool in accordance with an embodiment of the present invention.

FIG. 3 is a diagrammatic system block diagram of a handheld field maintenance tool in accordance with an embodiment of the present invention. It is preferred that tool 52 comply with at least one intrinsic safety specification, such as that listed above, in order to help ensure safety in potentially explosive environments. Handheld field maintenance tool 52 preferably includes at least one wireless process communication module 121. Suitable examples for wireless process communication module 121 include a module that generates and/or receives proper signals in accordance with a known wireless communication protocol, such as the WirelessHART protocol (IEC 62591). Another wireless process communication protocol is set forth in ISA100.11a. While FIG. 3 shows a single wireless process communication module 121, it is expressly contemplated that any suitable number of wireless process communication modules can be used to communicate in accordance with various wireless process communication protocols now in existence or later developed.

Handheld field maintenance tool 52 also includes at least one secondary wireless communication protocol module 123. Wireless communication protocol module 123 can communicate in accordance with one or more of the options shown in phantom in FIG. 3. Specifically, wireless communication protocol module 123 may communicate in accordance with a Bluetooth specification 124 (such as Bluetooth Specification 2.1 rated at Power Class 2; a Wi-Fi specification 126 (such as IEEE 802.11.a/b/g/n); a known RFID specification 128; cellular communication techniques 130 (such as GSM/CDMA); and/or satellite communication 132. These communication techniques and methodologies allow handheld field maintenance tool 52 to communicate directly with a wireless gateway or other suitable device either via direct wireless communication, or using the Internet. While one wireless communication protocol module 123 is shown in FIG. 3, any suitable number may be used. Each of the wireless process communication protocol module 121 and wireless communication protocol module 123 is coupled to controller 130 which is also coupled to the wired process communication module 138. Controller 130 is preferably a microprocessor that executes a sequence of instructions stored therein, or in memory coupled to controller 130, to perform handheld field maintenance tasks. Wired process communication module 138 allows handheld field maintenance tool 52 to be physically coupled via a wired connection at terminals 142, 144 to a field device. Examples of suitable wired process communication include the highway addressable remote transducer (HART®) protocol, the FOUNDATION™ Fieldbus protocol, Profibus and others.

Handheld field maintenance tool 52 includes a user interface module 156 for generating a user interface using display 120 and keys 122. Module 156 can include suitable display driver circuitry 158 and/or memory to interact with display 120. Module 156 also includes input circuitry 160 which is configured to interact with buttons 122 to receive user input. Additionally, in embodiments where display 120 includes a touchscreen, module 160 can include circuitry to generate user input data to controller 130 based upon a user's touch and/or gestures received by the touchscreen.

Handheld field maintenance tool includes or is coupled to camera 157. Preferably camera 157 is an internal component of handheld field maintenance tool 52. However, embodiments of the present invention do include camera 157 being a separate intrinsically-safe external module, such as that described below with respect to FIGS. 4 and 5. Preferably, camera 157 is a known CCD (Charge Coupled Device) or CMOS Image Acquisition System. While it is preferred that camera 157 capture images (either still, video, or both) in the visible spectrum, some embodiments may include a camera that is sensitive to, or images, infrared radiation. Moreover, while embodiments of the present invention will generally be described with respect to a single camera, it is expressly contemplated that multiple such cameras could be used. For example, a first camera may be an internal component of handheld field maintenance tool 52 and be sensitive to the visible spectrum. A second camera 157 could be an intrinsically-safe external camera that transmits its image data to the handheld field maintenance tool using wireless communication. Further still, yet another external camera 157 could be configured to capture a video using high-speed image acquisition using a high frame rate (for example 1000 frames per second) to capture fleeting occurrences within a process installation.

Handheld field maintenance tool 52 can include a number of additional items that facilitate additional functionality. Specifically, tool 52 can include a position detection module, such as GPS module 150. GPS module 150 can be configured to additionally use the Wide Area Augmentation System (WAAS) for improved accuracy and/or can be configured to operate using differential GPS techniques as appropriate. Module 150 is coupled to controller 130 to provide controller 130 with an indication of the geographic position of tool 52. While position detection module 150 is preferably an internal component of tool 52, it may be external and communicatively coupled thereto using a suitable wireless or wired communication protocol, such as Bluetooth 124, RFID 128, et cetera. Further, while position detection module 150 is generally described as GPS module 150, other techniques for triangulating the position of the handheld field maintenance tool based upon relative strength of wireless communication with wireless transceivers having known fixed positions can be employed. Examples of such wireless triangulation techniques include triangulation of the position of handheld field maintenance tool 52 based upon communication with three or more fixed-position WiFi communication points, or access points. Further still, as set forth above, embodiments of the present invention may include the ability to employ one or more wireless process communication protocol modules, such as module 121.

Additionally, tool 52 also preferably comprises compass module 152 coupled to controller 130 such that tool 52 can indicate the direction in which it is pointing. Finally, tool 52 can also include tilt module 154 coupled to controller 130 to provide an indication to controller 130 relative to an angle of inclination of tool 52 relative to gravity. However, additional axes of sensing are also contemplated.

The positional location module 150, compass module 152 and tilt module 154 are particularly useful where a handheld field maintenance tool helps a technician or engineer find the physical location of a wireless field device in the field. An oil refinery is often a very large process installation with many field devices positioned at various locations, some of which may not be readily visible. Position detection module 150 preferably provides position information to controller 130 such that images and/or video acquired by the handheld field maintenance tool is stored with meta data indicative of the geographic position of the handheld field maintenance tool when the image or video was acquired. Moreover, the compass heading is also preferably stored in the image or video metadata.

When a technician is out in the field, it may sometimes be useful for the technician to have the ability to either view a picture of a field device in its location (for the purposes of identification or to compare historical pictures to a current view) or to compare the noise generated by the device (a motor, for example) to that previously recorded. In accordance with an embodiment of the present invention, an intrinsically safe handheld field maintenance tool includes, or is operably coupled to, a video and/or audio input device that provides the ability to record audio and/or photo/video of a field device. Moreover, the handheld field maintenance tool is configured, through hardware, software, or a combination thereof, to associate the recorded audio and/or video of a field device with other device information, such as a device tag, geographic position, et cetera.

Figure 4:
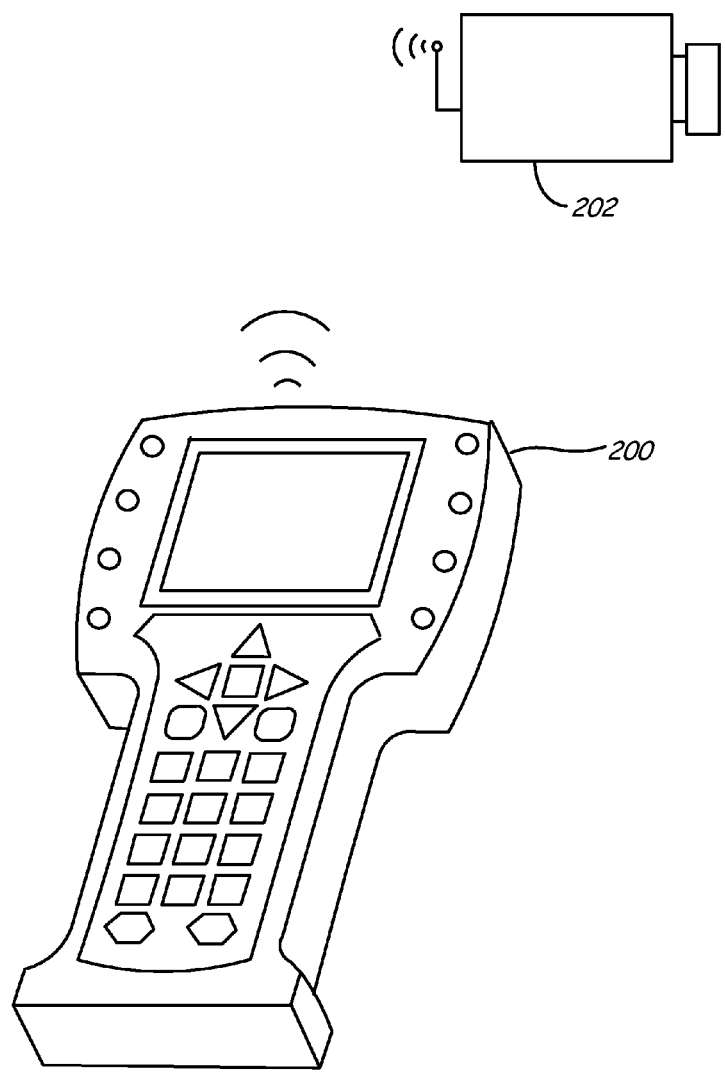
FIG. 4 is a diagrammatic view of an intrinsically safe handheld field maintenance tool interacting with an intrinsically safe camera/input device in accordance with an embodiment of the present invention.

FIG. 4 is a diagrammatic view of an intrinsically safe handheld field maintenance tool 200 interacting, wirelessly, with an intrinsically safe camera/input device 202. Preferably, handheld field maintenance tool 200 and external input device 202 communicate in accordance with one of the wireless communication technologies set forth with respect to FIG. 3. More preferably, the communication is in accordance with either Bluetooth communication, or WiFi communication. Wireless communication is preferred over wired communication since wireless communication does not have wired connection ports, and thus facilitates compliance with intrinsic safety requirements. Input device 202 may be a photographic camera that is able to capture one or more still images in the field. Alternatively, or additionally, device 202 may be a video camera capable of capturing and storing/streaming, or otherwise communicating video and corresponding audio information. Device 202 may also be a high-speed camera to capture fleeting process events. Further still, embodiments where the camera or the input device 202 is external to handheld field maintenance tool 200 are particularly useful in situations where a technician cannot easily view a given area. In such circumstances, the input device can simply be placed in a convenient location for viewing, and the image or video information can be viewed on the technician's handheld field maintenance tool. Moreover, embodiments of the present invention also contemplate a single handheld field maintenance tool simultaneously communicating with a plurality of such external input devices 202. In this manner, a technician viewing display 120 is able to simultaneously monitor conditions at a plurality of locations in the field. While the embodiment described above with respect to FIG. 4 employs wireless communication between the camera/input device 202 and the handheld field maintenance tool, embodiments of the present invention can be practiced where camera/input device 202 is physically coupled to the handheld field maintenance tool. In such instances, communication therebetween would preferably be via wired communication, such as through a Universal Serial Bus (USB) connection.

Figure 5:
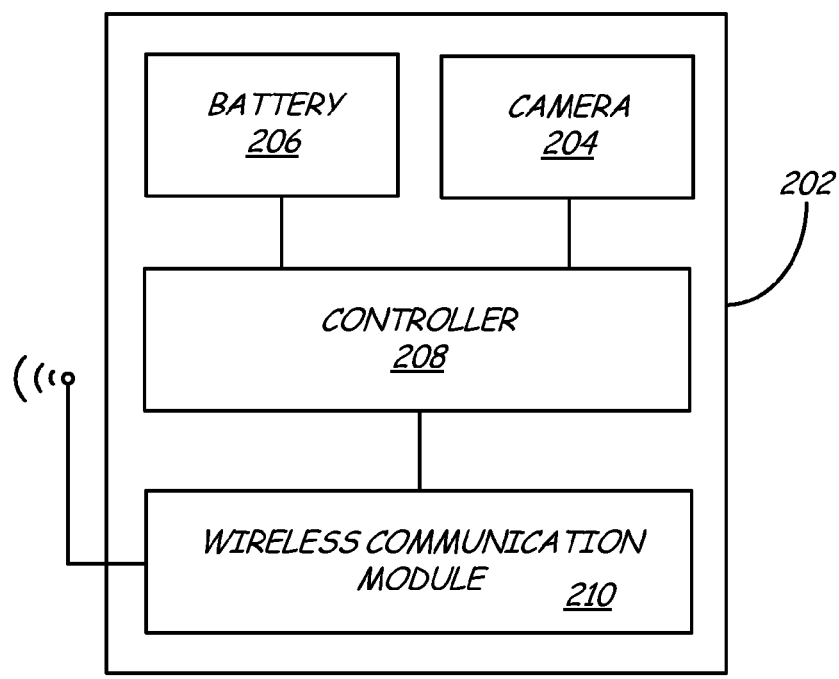
FIG. 5 is a block diagram of an external input module in accordance with an embodiment of the present invention.

FIG. 5 is a block diagram of external input module 202 in accordance with an embodiment of the present invention. Module 202 includes camera subsystem 204 which may be a known CCD (Charge Coupled Device) or CMOS image acquisition system. Preferably, input device 202 is powered by an internal battery 206 that may be rechargeable. Input device 202 preferably includes a controller 208, which is preferably a microprocessor. Controller 208 includes, or is coupled to, suitable memory to contain a number of program instructions to execute the functions of image acquisition, video or photo streaming, image or photo transfer, or other suitable functions. Additionally, the memory preferably includes sufficient capacity to store a substantial number of individual images, and/or videos. Input device 202 also includes a wireless communication module 210 which preferably operates in accordance with either a Bluetooth specification or a WiFi specification. Both such specifications support high-speed data transfer over a relatively limited physical proximity, such as tens of meters.

Figure 6:
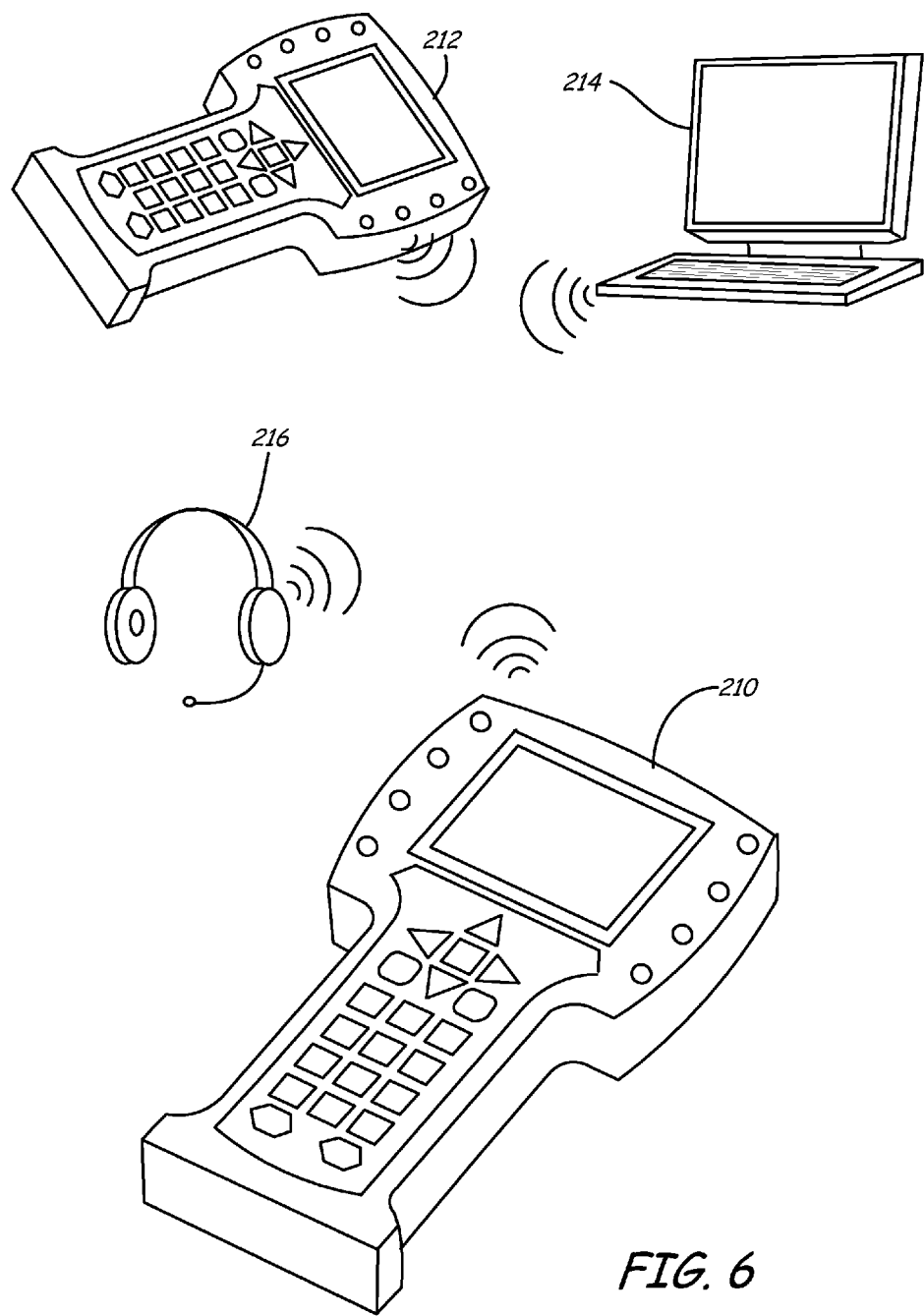
FIG. 6 is a diagrammatic view of handheld field maintenance tool receiving and/or sending previously-created audio/photo/video information from/to another handheld field maintenance tool or a personal computer in accordance with an embodiment of the present invention.

FIG. 6 is a diagrammatic view of handheld field maintenance tool 200 receiving and/or sending previously-created audio/photo/video information from/to another handheld field maintenance tool 212, or a personal computer 214, in accordance with an embodiment of the present invention. Handheld field maintenance tool 200 is also preferably capable of loading previously created audio/photo/video information from either another handheld field maintenance tool, or a personal computer. The previously-created audio/photo/video information could have been previously created by another handheld field maintenance tool, such as tool 214, created using another type or recording device, such as a digital camera, and stored on personal computer 214, et cetera. Handheld field maintenance tool 200 allows the technician to import this audio/video/photo information and associate such information with a field device's tag/unique identification such that the next time the handheld field maintenance tool 200 connects to the field device, the technician will be able to call up, or otherwise invoke the audio/photo/video information and view it on the display of the handheld field maintenance tool and/or listen to it on headset 216 communicating with the handheld field maintenance tool via Bluetooth. Moreover, the technician also has the ability to create new information and add it to the handheld, or otherwise associate it with the field device. Such new audio/photo/video information can also be uploaded to PC 214, handheld field maintenance tool 200 and/or maintained in a library for that field device. The audio/photo/video information could also be associated with one or more assets in an asset management system.

Figure 7:
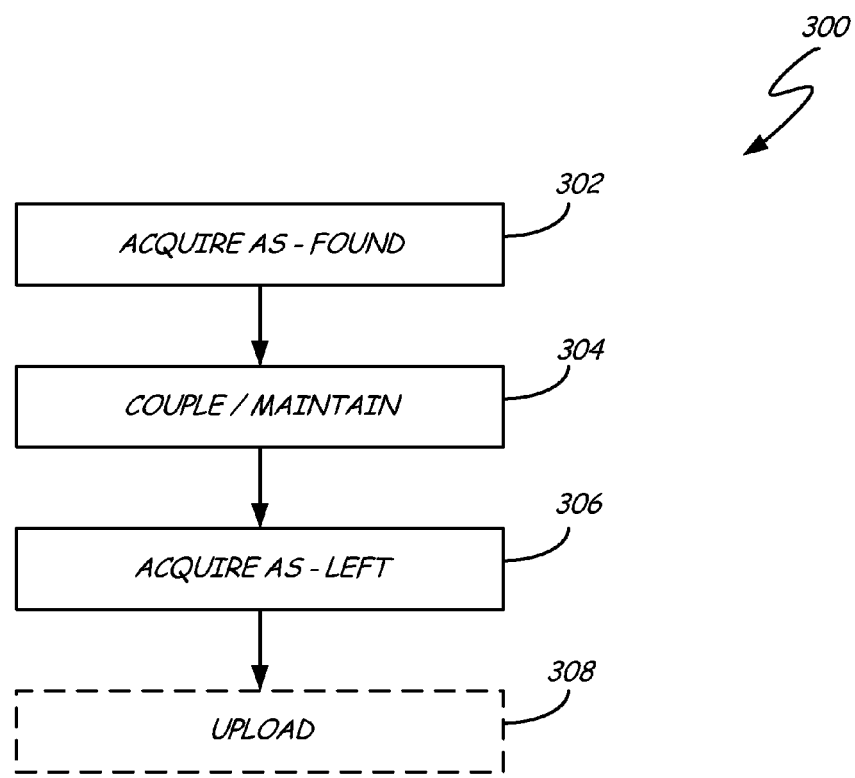
FIG. 7 is a flow diagram of a method of performing field maintenance using a handheld field maintenance tool in accordance with an embodiment of the present invention.

FIG. 7 is a flow diagram of a method of performing field maintenance using a handheld field maintenance tool in accordance with an embodiment of the present invention. Method 300 begins at block 302 where a technician employs a handheld field maintenance tool to acquire an image and/or video of a field device prior to working on the field device. This is an "as-found" image of the field device. There may be more than one as-found image. For example, multiple images or video from different views may be acquired. Additionally, multiple types of camera may be used for the as-found images. For example, a still camera may take an as-found high-resolution photo in the visible spectrum, and an as-found video may be acquired in the infrared spectrum.

Next, at block 304, the technician couples the handheld field maintenance tool to the field device and performs the require maintenance work, such as calibration, diagnosis, repair, et cetera. At block 306, the technician uses the handheld field maintenance tool to acquire the "as-left" image of the field device after the maintenance has been completed at block 304. Both the as-found and as-left images or videos are stored in the handheld field maintenance tool. Preferably, optional step 308 is executed where the as-found and as-left images or videos are uploaded to another device or system, such as an asset management system. In this way, field maintenance may be better documented. The archival of such images over time may also be useful for identifying wear or corrosion, or other conditions that occur slowly over time.

Although the present invention has been described with reference to particular embodiments, workers skilled in the art will recognize that changes may be made in form and detail without departing from the spirit and scope of the invention.

What is claimed is:

1. A handheld field maintenance tool comprising:
   a process communication module configured to communicatively couple to a field device and obtain a unique identification tag from the field device;
   a camera configured to obtain a first image and a second image relative to the field device;
   a wireless communication protocol module configured to communicatively couple to a wireless gateway;
   a global positioning system (GPS) module configured to determine a geographic location of the handheld field maintenance tool when the first image and the second image are obtained;
   a controller coupled to the process communication module and the wireless communication module, and operably coupled to the camera and the GPS module, the controller being configured to:
   acquire the first image from the camera,
   link the unique identification tag to the first image,
   store the first image in memory as an as-found image based on the unique identification tag,
   perform maintenance on the field device,
   acquire the second image from the camera,
   link the unique identification tag to the second image,
   store the second image in memory as an as-left image based on the unique identification tag,
   store the geographic location as metadata in the memory based on the unique identification tag,
   access a library using the wireless gateway,
   store the first image and the second image in the library based on the unique identification tag, and
   store the metadata in the library based on the unique identification tag.

2. The handheld field maintenance tool of claim 1, wherein the camera is an internal component of the handheld field maintenance tool.

3. The handheld field maintenance tool of claim 1, wherein the first image includes a first photograph of the entire field device and the second image includes a second photograph of the entire field device.

4. The handheld field maintenance tool of claim 1, wherein the camera is an external module, and wherein the handheld field maintenance tool and the camera communicate using short-range, high speed wireless communication.

5. The handheld field maintenance tool of claim 1, and further comprising:
   a compass module configured to determine a pointing direction of the handheld maintenance tool; and
   wherein the controller is operably coupled to the compass module and further configured to include the pointing direction with the metadata.

6. The handheld field maintenance tool of claim 1, and further comprising:
   a tilt module configured to determine an angle of inclination of the handheld maintenance tool; and
   wherein the controller is operably coupled to the tilt module and further configured to include the angle of inclination with the metadata.

7. A method of field maintenance using an intrinsically-safe handheld field maintenance tool, the method comprising:
   acquiring at least one as-found image relative to a field device;
   coupling the handheld field maintenance tool to the field device and performing at least one maintenance function on the field device;
   receiving a unique identification of the field device from the field device;
   acquiring at least one as-left image relative to the field device after completion of the at least one maintenance function;
   determining a geographic location of the handheld field maintenance tool when the at least one maintenance function is performed;
   determining a pointing direction of the handheld maintenance tool when the at least one maintenance function is performed;
   determining an angle of inclination of the handheld maintenance tool when the at least one maintenance function is performed;
   storing the at least one as-found image and the at least one as-left image based on the unique identification;
   storing the geographic location, the pointing direction, and the angle of inclination as metadata relating to the field device; and
   wherein the intrinsically-safe handheld field maintenance tool complies with at least one intrinsic safety specification such that it will not generate a source of ignition even under fault conditions.

* * * * *